United States Patent [19]

Berg et al.

[11] Patent Number: 5,545,764
[45] Date of Patent: Aug. 13, 1996

[54] PROCESS FOR THE CONTINUOUS PRODUCTION OF HIGH PURITY BISPHENOL A

[75] Inventors: Klaus Berg; Claus Wulff; Georg Malamet, all of Krefeld; Alfred Eitel, Dormagen, all of Germany; Kurt P. Meurer, Antwerpen, Belgium; Tony van Osselaer, St. Niklaas/Belsele, Belgium; Jürgen Hinz, Brasschaat, Belgium

[73] Assignee: Bayer Aktiengesellschaft, Leverkusen, Germany

[21] Appl. No.: 396,613

[22] Filed: Mar. 1, 1995

[30] Foreign Application Priority Data

Mar. 10, 1994 [DE] Germany ............... 44 08 008.5

[51] Int. Cl.[6] ................................................ C07C 37/68
[52] U.S. Cl. .................................................. 568/724
[58] Field of Search ................... 568/727, 754, 568/724

[56] References Cited

U.S. PATENT DOCUMENTS 5,269,887  12/1993  Jakob ...................................... 570/724
5,300,700  4/1994  Malamet et al. .

FOREIGN PATENT DOCUMENTS 4213872  11/1993  Germany .

Primary Examiner—Alan Siegel
Attorney, Agent, or Firm—Connolly & Hutz

[57] ABSTRACT

The present invention provides a process for the production of high purity bisphenol A by special in-process-crystallisation of bisphenol A/phenol adduct crystallisates.

2 Claims, No Drawings

PROCESS FOR THE CONTINUOUS PRODUCTION OF HIGH PURITY BISPHENOL A

The present invention relates to a process for the production of high purity bisphenol A (BPA) which contains less than 0.2 wt. % impurities. Thermally and colour stable bisphenol A produced in this manner improves the thermal colour stability of polymers produced from it, such as for example polycarbonate.

The production of high purity bisphenol A is known (for example DE-A 42 13 872). This document describes how manufactured bisphenol A may be brought to a degree of purity of 99.91 wt. %. The Hazen colour value may, however, be still further improved.

It has now been found that bisphenol A may be produced on an industrial scale with a high degree of purity and a good Hazen colour value. The high purity of the end product p,p-bisphenol A is almost entirely determined by BPA/phenol adduct in-process-crystallisation.

The present invention thus provides a process for recovering bisphenol A of a purity of 99.75 to > 99.94 wt. % and with a Hazen colour value of 5 to 10 from the reaction solution obtained on production of bisphenol A from acetone and phenol in the presence of sulphonic acid ion exchangers optionally modified with mercaptoamines and/or thiazolidines and/or thiocarboxylic acids, characterised in that 1. the reaction solution is adjusted to a content of p,p-bisphenol A in phenol of 25 to 35 wt. % at a temperature of 65° to 75° C. and
2. is then fed at this temperature into an n-stage cascade of crystallisers connected in series with a number of crystallisation reactors of n > 1 and
3. is circulated in each crystallisation reactor at a circulation rate of at least 500 m$^3$/h with a residence time of the mixture in each crystallisation reactor of at least three hours and
4. a temperature gradient from 70° C. in the first crystallisation reactor (n=1) to 40° C. in the final crystallisation reactor n is arranged over the entire crystallisation cascade and
5. p,p-bisphenol A adduct crystallisate with a p,p-BPA content of approximately 60% and a phenol content of approximately 40% is introduced into the crystal reactors, then filtered out, phenol removed and p,p-bisphenol recovered in a customary manner.

The modified sulphonic acid ion exchangers which may be used as catalysts in the process according to the invention are known (for example DE-A 37 27 641, corresponding to U.S. Pat. No. 4,912,263).

The reaction solution is adjusted (for example inter alia by weighing out, metering valves) to a content of bisphenol A in phenol of 25 to 35 wt. %, which may, for example, be determined by gas chromatography.

The phenolic bisphenol A solution obtained from reacting phenol and acetone is introduced into a multi-stage crystallisation cascade for crystallisation of the 1:1 bisphenol A/phenol adduct. The cascade used according to the invention has two or three crystallisers (n=2, 3), but may however also have more (n>3). The product drawn off from this cascade is filtered and the filtered out bisphenol A/phenol mixed crystals (1:1 adduct) are separated by desorption in phenol and bisphenol A, which product occurs as crystalline flakes.

The crystalliser cascade has at least two crystallisers (crystalliser n, n>1). Three to six crystallisers are advantageously connected in series.

The temperature is controlled such that over the entire crystallisation cascade there is arranged a temperature range from 70 (reactor inlet, reactor n=1) to 40° C. The first crystalliser (n=1) is operated at a maximum temperature of 70° C. and a temperature of 40° C. is reached in the final crystalliser n.

The bisphenol A is then separated in a customary manner. It has a degree of purity of at least 99.75 wt. % bisphenol A and a Hazen colour value of 5 to 10.

The particular feature of this special adduct crystallisation is that high purity BPA (> 99.94%) may be recovered by means of an improvement to in-process crystallisation without an additional crystallisation stage subsequent to the BPA process in which a BPA melt is recrystallised in a solvent (such as phenol or toluene or methylene chloride or acetone).

BPA/phenol adduct crystallisation with subsequent filtration and desorption is more economic than a separate recrystallisation stage.

EXAMPLES

Example 1

22 m$^3$/h of a 28% phenolic bisphenol A solution were fed into a crystalliser at a temperature of 70° C. and cooled in the crystalliser to 54° C. The resultant, phenolic BPA/phenol mixed crystal slurry was continuously circulated at 1200 m$^3$/h. The mixed crystal slurry, which is at a temperature of 54° C., is discharged from the crystalliser and fed into a second crystalliser (22 m$^3$/h). The mixed crystal slurry is further cooled to 41° C. in the second crystalliser. The mixed crystal slurry is circulated in the second crystalliser at 1000 m$^3$/h. The mixed crystal slurry/solution is discharged from the second crystalliser at 22 m$^3$/h and introduced into a rotary filter. Here, approximately 5 tonnes of mixed crystals are filtered out, washed and dried. The filtrate has a residual bisphenol A content of 14%. The purity of the filtered and worked up bisphenol A finished product is 99.90% p,p-BPA, the colour value of the BPA flake product was 5–10 Hazen. The residence time of the mixed crystal slurry in the crystalliser cascade was 9 h.

Example 2

45 m$^3$/h of a 28% phenolic bisphenol A solution were fed into a crystalliser at a temperature of 70° C. and cooled in the crystalliser to 54° C. The resultant, phenolic BPA/phenol mixed crystal slurry was continuously circulated at 1200 m$^3$/h. The mixed crystal slurry, which is at a temperature of 54° C., was discharged from the crystalliser and fed into a second crystalliser (45 m$^3$/h). The mixed crystal slurry was further cooled to 41° C. in the second crystalliser. The mixed crystal slurry was circulated in the second crystalliser at 1000 m$^3$/h. The mixed crystal slurry/solution was discharged from the second crystalliser at 45 m$^3$/h and introduced into a rotary filter. Here, approximately 10 tonnes of mixed crystals were filtered out, washed and dried. The filtrate had a residual bisphenol A content of 14%. The purity of the filtered and worked up bisphenol A finished product was 99.75% p,p-BPA, the colour value of the BPA flake product was 10 Hazen. The residence time of the mixed crystal slurry in the crystalliser cascade was 4 h.

Example 3

8 m$^3$/h of a 32% phenolic bisphenol A solution were fed into a crystalliser at a temperature of 70° C. and cooled in the crystalliser to 54° C. The resultant, phenolic BPA/phenol mixed crystal slurry was continuously circulated at 500 m³/h. The mixed crystal slurry, which is at a temperature of 54° C., is discharged from the crystalliser and fed into a second crystalliser (8 m³/h). The mixed crystal slurry is further cooled to 41° C. in the second crystalliser. The mixed crystal slurry is circulated in the second crystalliser at 550 m³/h. The mixed crystal slurry is discharged from the second crystalliser at 8 m³/h and introduced into a rotary filter. Here, approximately 2.0% of mixed crystals are filtered out, washed and dried. The purity of the filtered and worked up bisphenol A finished product is 99.94% p,p-BPA, the colour value of the BPA flake product was 5 Hazen. The residence time was approximately 20 h.

Example 4

10 m³/h of a 29% phenolic bisphenol A solution were fed at 72° C. into the first of three crystallisers and cooled to 56° C. The resultant phenolic bisphenol A/phenol mixed crystal slurry was here circulated at 1000 m³/h. The first crystalliser ran over into a second crystalliser maintained at 49° C. Cooling was again achieved by a circulation rate of 1000 m³/h. Finally, the mixture was cooled to a final temperature of 41° C. in the third crystalliser. The resultant bisphenol A/phenol mixed crystals were separated in a customary manner in a rotary filter and worked up to yield pure bisphenol.

The purity of the bisphenol produced was 99.92% and the colour value 5–10 Hazen. Total residence time in the crystalliser cascade was 18 h.

Comparative example 1 (operation with a single crystalliser)

The same process is used as in example 2 with the difference that the first crystalliser was not operated at a temperature of 54° C. All other processing parameters remain the same. The purity of the filtered and worked up bisphenol A finished product was 99.52% p,p-BPA, the colour value of the flake product is 30. The residence time of the mixed crystallisate in crystalliser 2 ($T=41°$ C.) was approximately 2 h.

Comparative example 2 (operation with 2 crystallisers, but both adjusted to 41° C.)

The same process is used as in example 2. All processing parameters remain the same, only the temperature of crystalliser 1 is reduced to 41° C.

The purity of the filtered and worked up bisphenol A finished product was 99.62% p,p-BPA, the colour value of the flake product is 25. The residence time of the mixed crystallisate in both crystallisers ($T_1=41°$ C., $T_2=41°$ C.) was 4 h.

We claim:

1. A process for recovering bisphenol A of a purity of 99.75 to > 99.94 wt. % and with a Hazen color value of 5 to 10 from the reaction solution obtained on production of bisphenol A from acetone and phenol in the presence of sulphonic acid ion exchangers, wherein 1) the reaction solution is adjusted to a content of p,p-bisphenol A in phenol of 25 to 35 wt. % at a temperature of 65° to 75° C.; and 2) is then fed at this temperature into an n-stage cascade of crystallizers connected in series with a number of crystallization reactors of n>1; and 3) is circulated in each crystallization reactor at a circulation rate of at least 500 m³/h with a residence time of the mixture in each crystallization reactor of at least three hours; and 4) a temperature gradient from 70° C. in the first crystallization reactor to 40° C. in the final crystallization reactor is arranged over the entire crystallization cascade; and 5) p,p-bisphenol A adduct crystallisate with a p,p-BPA content of approximately 60% and a phenol content of approximately 40% is precipitated inside the crystallization reactors, then filtered out, phenol is removed and p,p-bisphenol is recovered.

2. The process as claimed in claim 1, wherein the sulfonic acid ion exchangers are modified with one or more of mercaptoamines, thiazolidines or thiocarboxylic acids.

* * * * *